US006974455B2

(12) United States Patent
Garabedian et al.

(10) Patent No.: US 6,974,455 B2
(45) Date of Patent: Dec. 13, 2005

(54) AUTO ADVANCING RADIO FREQUENCY ARRAY

(75) Inventors: Robert J. Garabedian, Tyngsboro, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 39 days.

(21) Appl. No.: 10/121,113

(22) Filed: Apr. 10, 2002

(65) Prior Publication Data

US 2003/0195502 A1    Oct. 16, 2003

(51) Int. Cl.[7] ............................................. A61B 18/18
(52) U.S. Cl. ........................................ 606/41; 607/101
(58) Field of Search ....................... 606/41, 42, 45–50; 607/101, 102

(56) References Cited

U.S. PATENT DOCUMENTS

| 5,222,953 | A | * | 6/1993 | Dowlatshahi ................ 606/15 |
| 5,370,675 | A | * | 12/1994 | Edwards et al. ............ 607/101 |
| 5,472,441 | A | * | 12/1995 | Edwards et al. ............. 606/41 |
| 5,536,267 | A | * | 7/1996 | Edwards et al. ............. 606/41 |
| 5,551,426 | A |  | 9/1996 | Hummel et al. |
| 5,951,547 | A |  | 9/1999 | Gough et al. |
| 6,010,476 | A | * | 1/2000 | Saadat ........................ 604/22 |
| 6,080,150 | A | * | 6/2000 | Gough ........................ 606/41 |
| 6,090,105 | A | * | 7/2000 | Zepeda et al. .............. 606/41 |
| 6,221,071 | B1 | * | 4/2001 | Sherry et al. ............... 606/41 |
| 6,231,570 | B1 |  | 5/2001 | Tu et al. ..................... 606/41 |
| 6,330,478 | B1 |  | 12/2001 | Lee et al. |
| 6,428,538 | B1 | * | 8/2002 | Blewett et al. .............. 606/46 |
| 6,461,351 | B1 | * | 10/2002 | Woodruff et al. ........... 606/32 |
| 6,482,203 | B2 | * | 11/2002 | Paddock et al. ............. 606/41 |
| 6,497,704 | B2 | * | 12/2002 | Ein-Gal ...................... 606/41 |
| 2002/0026185 | A1 |  | 2/2002 | Gough |
| 2002/0120261 | A1 | * | 8/2002 | Morris et al. ............... 606/41 |

FOREIGN PATENT DOCUMENTS

EP          0 861 676 A2    9/1998

* cited by examiner

*Primary Examiner*—Michael Peffley
(74) *Attorney, Agent, or Firm*—Bingham McCutchen LLP

(57) ABSTRACT

A system for ablating lesions in the interior regions of the human body including a RF catheter and a control system adapted to facilitate the automatic step deployment of an array-type energy delivery system positioned within the catheter. The RF catheter and control system further include an auto array deployment mechanism coupled to the array-type energy delivery system and an impedance and temperature monitoring system. In addition, the system includes a probe positioning device adapted to maintain a RF probe in a desired orientation during ablation procedures.

16 Claims, 5 Drawing Sheets

AUTO ADVANCING RADIO FREQUENCY ARRAY

FIELD OF THE INVENTION

The present invention relates to systems and methods for ablating tissue in interior regions of the human body and, more particularly, to systems and methods that facilitate the automatic deployment and placement of a needle array for precise lesion ablation.

BACKGROUND OF THE INVENTION

Thermal coagulation of tissue using RF energy is frequently being used to treat maladies within the body such as liver tumor lesions. Physicians frequently make use of catheter-based RF systems to gain access to interior regions of the body. For treatment of large lesions, the catheter-based RF systems commonly employ needle array-type energy delivery devices. However, depending on the size of the lesion to be ablated and, thus, the size of the array used to ablate the lesion, many conventional systems experience difficulty providing an adequate amount of current to cause tissue heating and coagulation. To address this problem, many manufacturers simply supply a larger generator to provide an adequate amount of current to cause tissue heating and coagulation. Others address the large array problem by having the user step deploy their array at a measured and stable rate. In such a procedure, the physician must carefully apply ablating energy to the element for transmission to the tissue to be ablated, at each predetermined distance, for a fixed period of time and/or until the tissue reaches a desired temperature. A heated center is created as a result, which further heats the target region when the array is fully deployed. This manual procedure tends to be confusing because of the multiple parameters that need to be observed prior to moving on to the next deployment location.

Physicians may experience other difficulties when the lesion to be ablated is close to the dermis or is in tissue that is light in density. When RF catheters or probes are pushed into dense body tissue such as the liver, the probes tend to be inserted deeply enough to remain upright during ablation. However, when ablation procedures, including ablation of some liver lesions, are performed relatively close to the dermis or are performed in tissue that is especially light in density, such as the lung, the physician may have a difficult time maintaining the catheter or probe in its initial orientation. As a result, the physician must either stack pads or gauze under the probe or hold the probe in place during the entire ablation procedure, which is typically about 6–15 minutes. If the physician chooses not to hold or support the probe during such procedures, the probe may sag and could push the energy delivery needles or tines into the dermis layer or other tissue areas not meant to be ablated.

Thus, a need exists for controlling the advancement of the needle array such that the array moves forward to contact new tissue areas once the tissue area presently in contact is ablated. In addition, a need exists for maintaining the probe in a desired orientation for a hands-free mode of operation for the physician.

SUMMARY OF THE INVENTION

The present invention is directed to improved systems and methods that facilitate the automatic deployment and placement of a needle array for precise ablation of body tissue using RF energy. The RF ablation system of the present invention tends to eliminate any confusion as to when the needle array should be farther deployed into the tissue during step deployment ablation procedures, minimize the time to carry out such procedures, and eliminate the need for insertion track bleeding management techniques following such procedures. In one innovative aspect of the present invention, a needle array-type energy delivery system is automatically advanced or step deployed under temperature and/or impedance feedback control. In another innovative aspect of the present invention, a catheter based RF ablation system includes an auto array deployment or advancement system which may comprise a servo, an electromagnetic, an electro-pneumatic, a hydraulic, or the like, actuating mechanism, or a stepper motor. In a preferred embodiment of the present invention, a catheter based RF ablation system includes a catheter having an elongate tube and a handle connected to the tube, a needle array slidably received in the tube and handle, a servo actuated drive mechanism mounted in the handle and coupled to the needle array, and a control system coupled to the servo actuated drive and needle array. The control system preferably comprises a RF energy source, a drive controller, and a temperature and/or impedance monitoring module for step deployment at predetermined temperature and/or impedance values. The control system may also include a timer for step deployment at predetermined intervals.

In operation, the catheter is inserted through intervening tissue until it reaches a treatment site, such as a tumor lesion within the liver, where the needle array is initially manually deployed to a first fixed diameter. The RF power source is activated to a preferred power level while the temperature/impedance monitoring module of the control system simultaneously monitors the temperature and/or impedance measurements coming from the needle array. Once a predetermined temperature and/or impedance is achieved, the drive controller activates the servo actuated drive mechanism to advance the needle array further into the tissue to be ablated. Alternatively, the drive controller activates the servo actuated drive mechanism to advance the needle at predetermined intervals. This active advancing process is repeated, until the array is fully deployed. Once fully deployed, the needle array acts in accordance with conventional ablation procedures.

In another embodiment of the present invention, the system preferably includes a probe positioning device capable of maintaining the RF ablation probe in a desired orientation and preventing the ablation of tissue not meant to be ablated. The probe positioning device preferably comprises a probe holder adapted to slidably receive a RF probe and supports connected to the probe holder. The probe holder being adapted to receive a RF probe.

Further objects and advantages of the present invention will become more apparent from the following detailed description taken with the following drawings.

DESCRIPTION OF EXEMPLARY EMBODIMENTS

Figure 1:
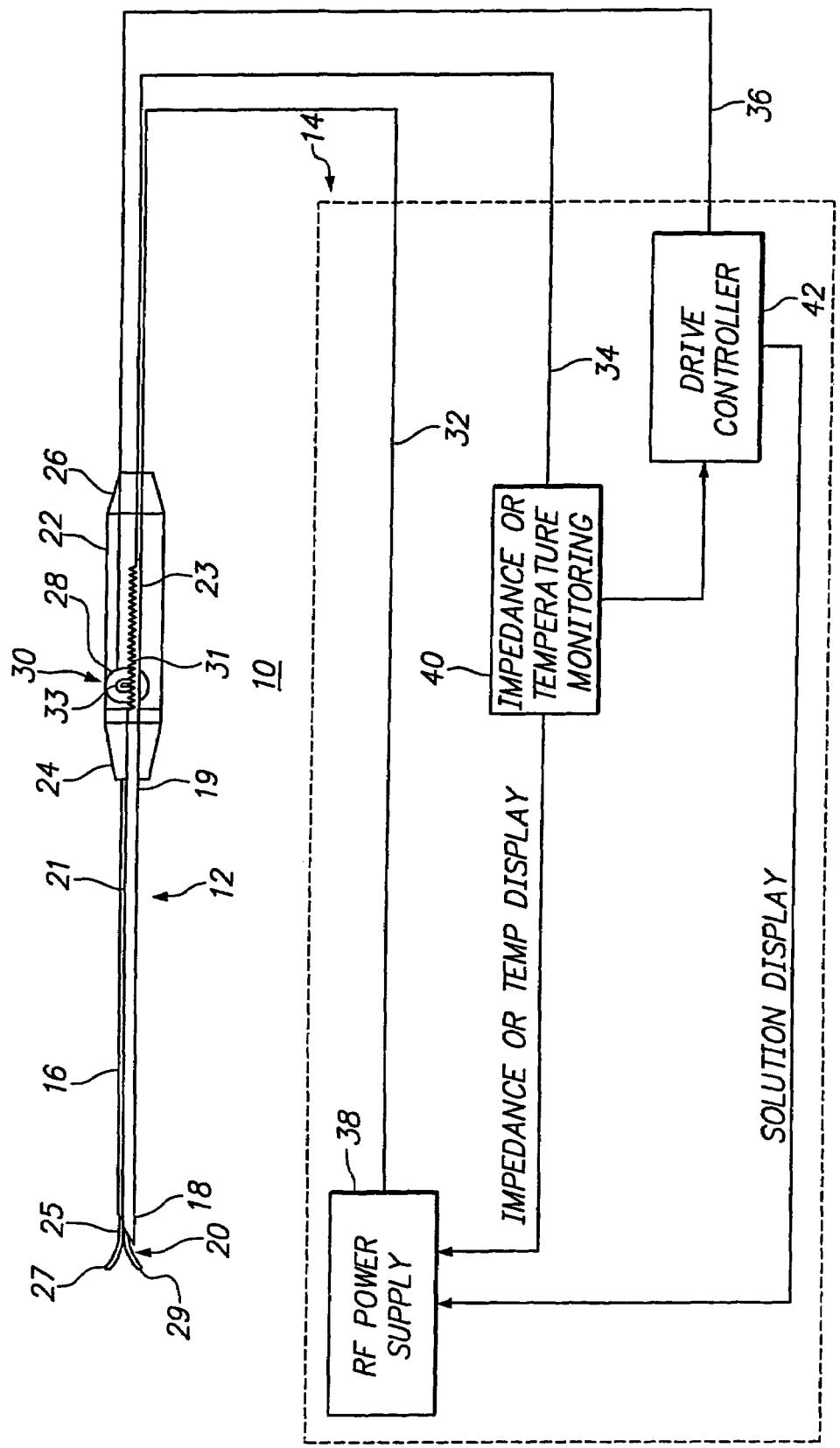
FIG. 1 shows a plan view of a representative system of the present invention at a partially deployed state comprising a RF catheter connected to a control system.

Referring in detail to the drawings, an illustrated embodiment of an improved RF ablation system of the present invention is shown. Turning to FIG. 1, the illustrated embodiment shows an overall view of a RF ablation system (10) of the present invention comprising a RF probe or catheter (12) connected to a control system (14). The RF catheter (12) preferably comprises an elongate tube (16) having distal and proximal ends (18) and (19) and a handle (22) having distal and proximal ends (24) and (26). The distal end (24) of the handle (22) is connected to the proximal end (19) of the tube (16). A passageway (not shown) extends through the tube (16) and handle (22). A needle array (20) having an elongate shaft (21) is preferably slidably received in the passageway with a proximal end (23) extending into the handle (22) and a distal end (25) extending to the distal end (18) of the tube (16) when in a retracted state and, as the illustrated embodiment shows, beyond the distal end (18) of the tube (16) when deployed. The distal end (25) of the shaft (21) of the needle array (20) preferably splits to form an array of individual tines or needle electrodes (27) and (29) that are deployable in opposite directions to maximize ablation lesion size. The tines or needles (27) and (29) are preferably pre-stressed or pre-bent in a manner known in the art such that when unrestrained, i.e., deployed beyond the distal end of the catheter (12), the needles (27) and (29) return to their bent form.

Figure 2:
FIG. 2 shows a plan view of the RF catheter of the representative system at 25% deployment.
Figure 3:
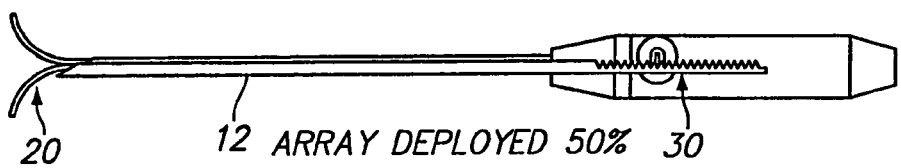
FIG. 3 shows a plan view of the RF catheter of the representative system at 50% deployment.
Figure 4:
FIG. 4 shows a plan view of the RF catheter of the representative system at 75% deployment.
Figure 5:
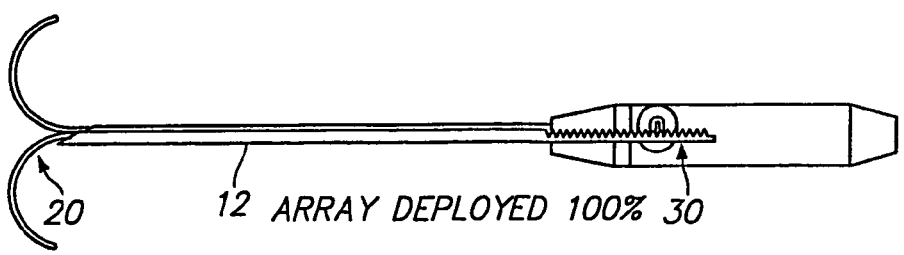
FIG. 5 shows a plan view of the RF catheter of the representative system at 100% deployment.

Turning to FIGS. 2–5, the needle array (20) of the catheter (12) is shown with the tines or needle electrodes (27) and (29) at different stages of deployment. FIG. 2 shows the needle array (20) at a deployment state of 25%. FIG. 3 shows the needle array (20) at a deployment state of 50%. FIG. 4 shows the needle array (20) at a deployment state of 75%. FIG. 5 shows the needle array (20) at a deployment state of 100%.

As depicted in FIG. 1, the catheter (12) further includes an auto array deployment or advancement system (30) adapted to deploy or retract the individual needles (27) and (29) at the distal end (25) of the needle array (20). The deployment system (30) preferably includes a rack or screw drive (31), or some other driven gear, preferably attached to or formed on the proximal end (23) of the shaft (21) of the needle array (20), and a driver (28) mounted in the handle (22) toward its distal end (24). The driver (28) preferable includes a servo motor (not shown) and a driving gear (33), such as a spur gear, screw gear, worm gear, or the like, that is operably coupled to the screw or rack drive (31) on the needle array (20). Alternatively, the driver (28) may include a stepper motor or an electromagnetic, electro-pneumatic, hydraulic, or the like, actuating mechanism. The driver (28) or some other apparatus (not shown) incorporated into the handle (22) of the catheter (12) and connected to the needle array (20) may be manually manipulated to deploy or retract the needles (27) and (29) to a desired position. The catheter (12) may also include mechanical stops or detents located internally within the handle (22) that provide the user with tactile feel as to the positioning of the needles (27) and (29) when they are manually advanced.

For example, such tactile feel may be provided by a spring plunger with a ball detent built into the handle (22) wherein the spring loaded ball would ride along a smooth wall of an inner handle. Recess or detent locations would be calibrated along the inner handle to deploy the array a predetermined diameter. Alternatively, a tab or o-ring connected to the inner surface of an outer handle could be used to locate recesses or detents formed on the inner handle. Another alternative may include radial grooves on an inner or outer handle that enables the probe to be rotated and held in place after the array has been deployed a predetermined diameter.

The control system (14) preferably comprises a RF power source (38), such as a generator, a drive controller (42) coupled to the power source (38), an impedance and/or temperature monitoring module (40) coupled to the power source (38) and the drive controller (42), and a variety of displays to indicate temperature, impedance, needle position, elapsed time, and the like. The drive controller (42) may be built into the RF generator or may be a stand alone unit. A first cable (32), interconnected to the power supply (38), extends from the control system (14) to the proximal end (23) of the shaft (21) of needle array (20) to supply RF power to the needles (27) and (29) of the needle array (20). A second cable (34), interconnected to the monitoring module (40), extends from the control system (14) to the proximal end (23) of the needle array (20) to communicate temperature or impedance measurements from the needles (27) and (29), which preferably include temperature and/or impedance measuring capabilities. A third cable (36), interconnected to the drive controller (42), extends from the control system (14) to the servo motor of the driver (28) in the handle (22) of the catheter (12) to control or actuate the driving gear (33), which in turn causes the deployment or retraction of the needle array (20).

The RF ablation system (10) of the present invention is preferably operated in a manner that increases the current density applied to the tissue to be ablated. The system (10) preferably uses impedance or temperature feedback to control the servo actuated array deployment mechanism (30) resulting in the automated step deployment of the needle array (20). Because the deployment of the needle array (20) is fully automated, any confusion associated with conventional step deployment methods used with conventional needle array-type devices tends to be eliminated.

In operation, the distal end (18) of the catheter (12) is inserted through intervening tissue until it reaches a treatment site, such as a tumor lesion within the liver. Once the distal end (18) of the catheter (12) is in place, the needle array (20) is preferably manually deployed to extend the needles (27) and (29) to a first fixed diameter. If the device includes internal detents or steps, the needle array (20) is advanced until a step or detent is encountered. With return electrodes properly in place on the patient, the RF generator of the power source (38) is activated to a preferred power level while the temperature/impedance monitoring module (40) of the control system (14) simultaneously monitors the temperature and/or impedance measurements coming from the needles (27) and (29). Once a predetermined temperature and/or impedance is achieved, while RF power is still being delivered, the drive controller (42) of the control system (14) activates the servo motor of the driver (28) and, thus, actuates the driving gear (29) to advance the needle array (20) forward a predetermined distance and, thus, advance the needles (27) and (29) further into the tissue to be ablated. Alternatively, the needles (27) and (29) may be advanced further into the tissue to be ablated after a predetermined period of time has elapsed. This active advancing process is repeated, as shown in FIGS. 2–5, until the array (20) is fully deployed as shown in FIG. 5. Once the needle array (20) is fully deployed, the needle electrodes (27) and (29) act in accordance with conventional ablation procedures.

After completion of the ablation procedure, the needle array (20) may be automatically fully retracted into the elongate tube (16) of the catheter (12) prior to retrieval of the catheter (12). Alternatively, the needle array (20) may be retracted automatically to a partially deployed state in which the needles (27) and (29) extend slightly beyond the distal end (18) of the catheter (12). In the partially deployed state, the catheter (12) may be retrieved while the needle array (20) ablates the catheter insertion track to minimize or eliminate post procedure bleeding along the insertion track.

As indicated herein, the RF ablation system (10) of the present invention advantageously tends to 1) eliminate any confusion as to when the needle array (20) should be further deployed into the tissue, 2) minimize the time to carry out such procedures, and 3) eliminate the need for gelfoam or comparable insertion track bleeding management techniques.

Figure 6:
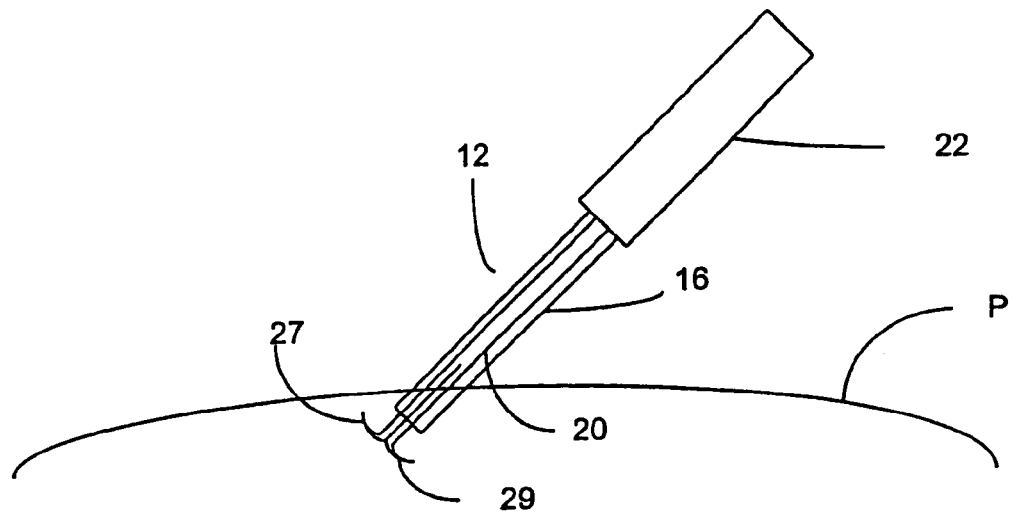
FIG. 6 shows a plan view of a RF probe with a set of tines deployed in a patient.

When RF probes, such as the catheter (12) of the present invention, are pushed into dense body tissue such as the liver, the probes tend to be inserted deeply enough to remain upright during ablation. However, some ablation procedures, including the ablation of some liver lesions, are performed relatively close to the dermis or may be performed in tissue that is especially light in density, such as the lung. As a result, the probe or catheter (12) may have a difficult time maintaining the orientation initially set up by the physician, requiring the physician to hold the probe in place during the entire ablation procedure, which is typically about 6–15 minutes, or stack pads or gauze under the probe to support the probe. If the physician chooses not to hold or support the probe during such procedures, the probe may sag and could push the needles (27) and (29) into the dermis layer or other tissue areas not meant to be ablated. For example, FIG. 6 shows the catheter (12) of the present invention inserted into a patient P at a relatively shallow depth with at least one of the tines (27) and (29) being deployed relatively close to the dermis of the patient P. If the catheter (12) were to sag, the energy delivery needles or tines may be pushed into the dermis layer or other tissue areas not meant to be ablated.

Figure 7:
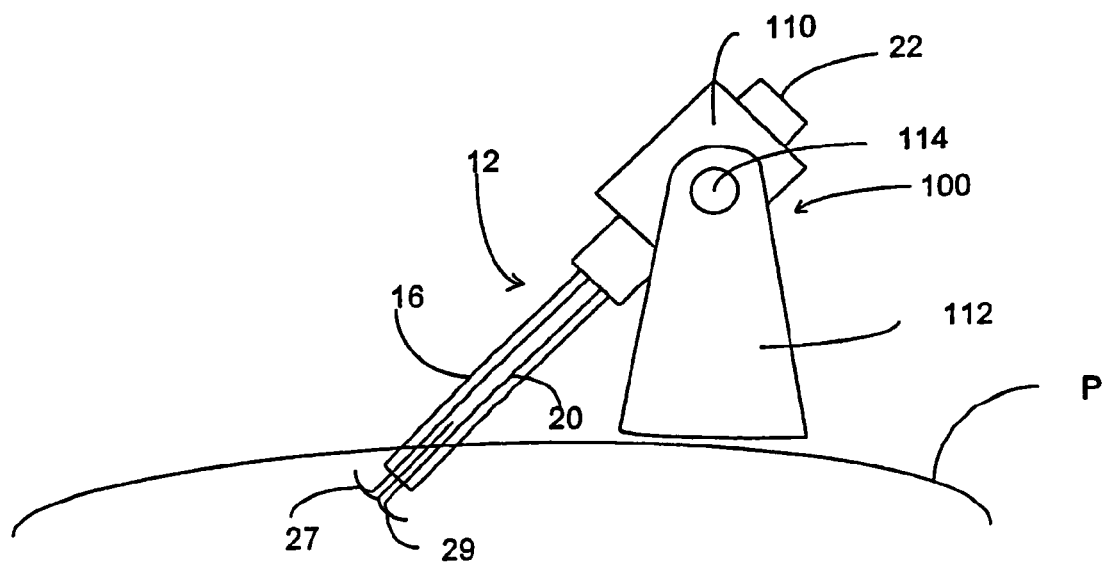
FIG. 7 shows a plan view of a probe holder of the present invention holding a RF probe with a set of tines deployed in a patient.
Figure 9:
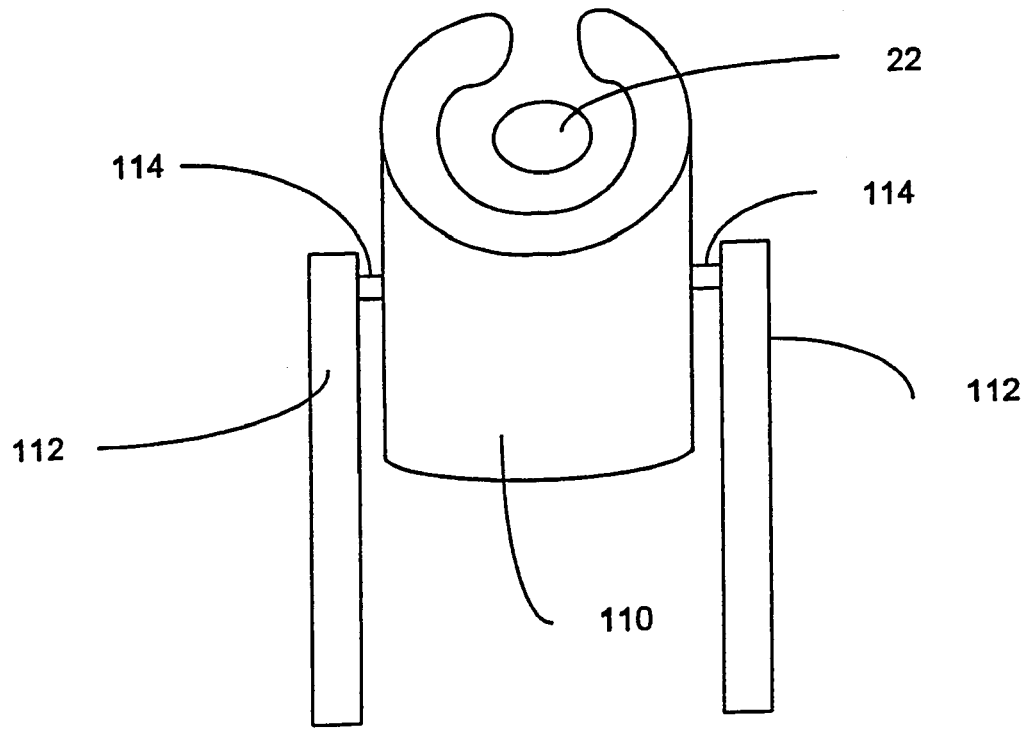
FIG. 9 shows a side view of the probe holder of the present invention.

To assist in the deployment of the RF catheter (12) of the present invention and avoid ablating tissue not meant to be ablated, the present invention further includes a probe positioning device (100). As depicted in FIG. 7, the probe positioning device (100) is capable of propping the catheter (12) up and holding it in a desired upright orientation. The positioning device (100) includes a holder (110) adapted to slidably receive the handle (22) of the catheter (12) and two side support members (112) adapted to rest on the patient P. As shown in FIG. 9, the holder (110) is pivotably connected to the support members (112) via a pair of protrusions or shafts (114) extending inwardly from the support members (112). The holder (110) and support members (112) have a friction fit or may include a ratchet mechanism or the like there between to releasably lock the holder (110) in a desired orientation.

Figure 8:
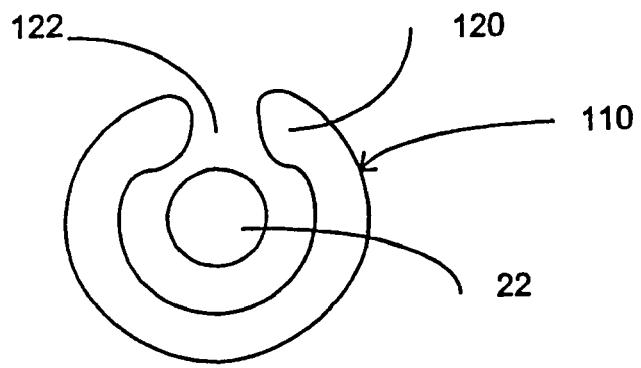
FIG. 8 shows an end view of the probe holder of the present invention.

As depicted in FIG. 8, the holder (110) includes a semi-annular body (120) having an opening (122) that is slightly smaller than the diameter of the handle (22) of the catheter (12) of the present invention. The body (120) of the holder (110) is preferably formed from a semi-compliant material to enable the handle (22) of the catheter (12) to snap into place within the holder (110).

Figure 10:
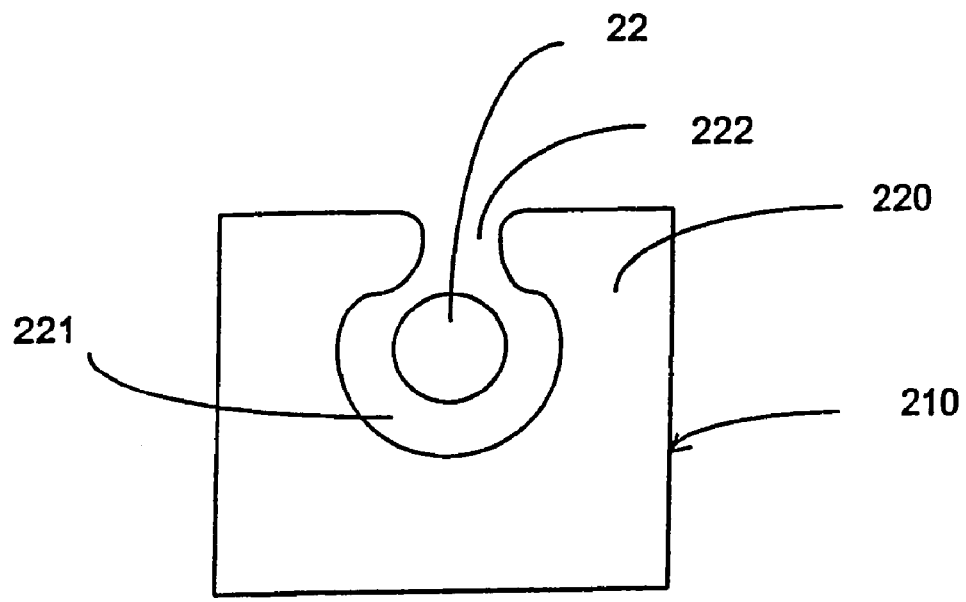
FIG. 10 shows an end view of an alternative embodiment of the probe holder of the present invention.
Figure 11:
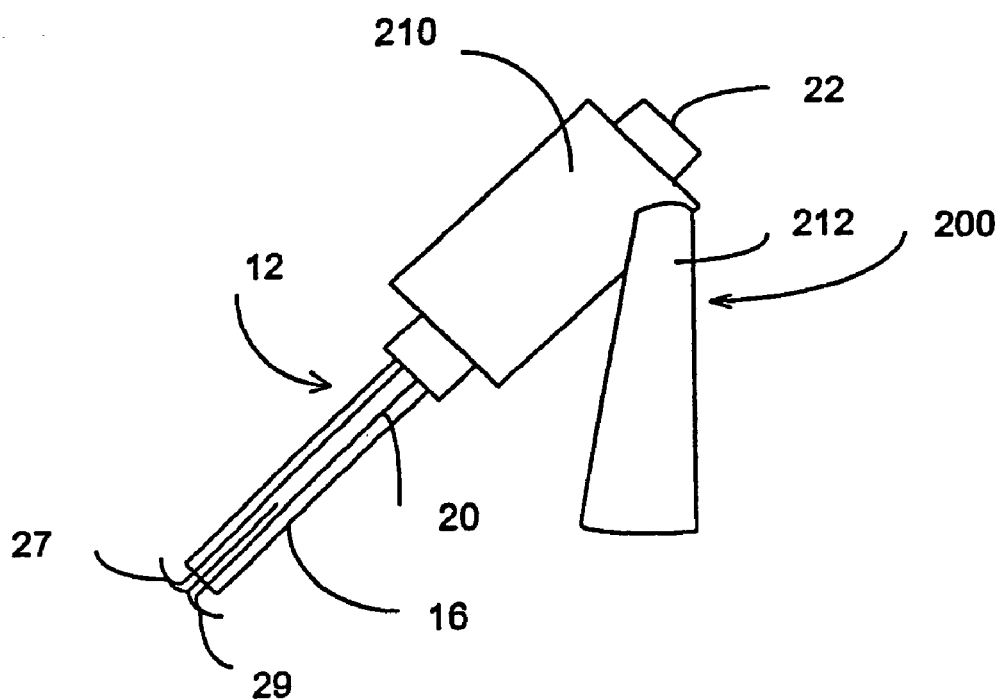
FIG. 11 shows a plan view of the alternative embodiment of the probe holder of the present invention.

In an alternative embodiment shown in FIGS. 10 and 11, the positioning device (200) may be fabricated as a thermoformed insert to be inserted into a thermoformed tray. The positioning device (200) includes a holder (210) and a support (212). The holder (210) includes a body (220) having a substantially circular passageway (221) adapted to slidably receive the handle (22) of the catheter (12) of the present invention. The body (220) further includes an opening (222) having a width that is slightly smaller than the diameter of the handle (22) to allow the handle (22) to be snapped into place within the passageway (221).

While the invention is susceptible to various modifications and alternative forms, specific embodiments thereof have been shown in the drawings and are herein described in detail. It should be understood, however, that the invention is not to be limited to the particular form disclosed, but to the contrary, the invention is to cover all modifications, equivalents, and alternatives falling within the spirit and scope of the appended claims.

What is claimed:

1. A radio frequency (RF) ablation system comprising:
an ablation probe including a handle, a deployable needle array, and an array deployment mechanism at least partially contained within the handle, and
a drive controller electrically coupled to the ablation probe, wherein the controller is configured to send control signals that prompt the array deployment mechanism to incrementally deploy the needle array in the distal direction at a plurality of positions, wherein the needle array is maintained at each position for a period of time that allows tissue to be effectively ablated when ablation energy is delivered to the needle array at the respective position.

2. The ablation system of claim 1 wherein the controller is configured to send control signals that prompt the array deployment mechanism to incrementally deploy the needle electrode array from a fully retracted position to a fully deployed position.

3. The ablation system of claim 1 further comprising a RF power supply electrically coupled to the ablation probe, wherein the RF power supply is configured to send RF energy to the needle array.

4. The ablation system of claim 1 further comprising a temperature or impedance monitoring module electrically coupled to the ablation probe, wherein the monitoring module is configured to receive tissue temperature or impedance measurements from the ablation probe, and wherein the controller is configured for sending the control signals in response to the tissue measurements.

5. The ablation system of claim 4 wherein the needle array is capable of measuring temperature or impedance.

6. The ablation system of claim 1 wherein each period of time is predetermined.

7. The ablation system of claim 1 wherein each position is predetermined.

8. A tissue ablation system comprising:
an ablation probe including a handle, a deployable ablative element, and an automatic deployment mechanism at least partially contained within the handle and mechanically coupled to the ablative element, and
a drive controller electrically coupled to the ablation probe, wherein the controller is configured to actuate the deployment mechanism to incrementally deploy the ablative element in the distal direction at a plurality of positions, wherein the ablative element is maintained at each position for a period of time that allows tissue to be effectively ablated when ablation energy is delivered to the needle array at the respective position.

9. The ablation system of claim 8 wherein the controller is configured to actuate the deployment mechanism to incrementally deploy the ablative element from a fully retracted position to a fully deployed position.

10. The ablation system of claim 8 further comprising an ablation source coupled to the ablation probe, wherein the ablation source is configured to send ablation energy to the ablative element.

11. The ablation system of claim 8 further comprising a temperature or impedance monitoring module electrically coupled to the ablation probe, wherein the monitoring module is configured to receive tissue temperature or impedance measurements from the ablation probe, and wherein the controller is configured for actuating the deployment mechanism in response to the tissue measurements.

12. The ablation system of claim 11 wherein the ablative element is capable of measuring temperature or impedance.

13. The ablation system of claim 8 wherein the deployment mechanism is configured to deploy the ablative element in response to control signals, and the drive controller is configured for sending the control signals to the deployment mechanism.

14. The ablation system of claim 8 wherein the ablative element comprises one or more electrodes.

15. The ablation system of claim 8 wherein each period of time is predetermined.

16. The ablation system of claim 8 wherein each position is predetermined.

* * * * *